(12) United States Patent
Shimmick et al.

(10) Patent No.: US 6,605,081 B1
(45) Date of Patent: Aug. 12, 2003

(54) SYSTEMS AND METHODS FOR IMAGING CORNEAL PROFILES

(75) Inventors: John K. Shimmick, Belmont, CA (US); Stephen J. Hinkson, San Francisco, CA (US); Charles R. Munnerlyn, San Jose, CA (US)

(73) Assignee: Visx, Incorporated, Santa Clara, CA (US)

( * ) Notice: Subject to any disclaimer, the term of this patent is extended or adjusted under 35 U.S.C. 154(b) by 0 days.

(21) Appl. No.: 09/565,774

(22) Filed: May 5, 2000

Related U.S. Application Data

(60) Division of application No. 09/083,773, filed on May 22, 1998, now Pat. No. 6,302,876, which is a continuation-in-part of application No. 08/863,665, filed on May 27, 1997.

(51) Int. Cl.[7] ............................................. A61F 9/007
(52) U.S. Cl. ................................ 606/10; 606/3; 606/5; 351/206; 351/207
(58) Field of Search ............................. 351/209–221; 606/3, 5, 10–13

(56) References Cited

U.S. PATENT DOCUMENTS

| 4,440,477 A | * | 4/1984 | Schachar | 351/212 |
| 4,721,379 A | * | 1/1988 | L'Esperance | 606/5 |
| 4,799,785 A | * | 1/1989 | Keates et al. | 351/212 |

FOREIGN PATENT DOCUMENTS

| SU | 1115715 | * | 9/1984 | 351/212 |
| SU | 1337042 | * | 9/1987 | 351/212 |

OTHER PUBLICATIONS

Hickson et al "A Comparison Between PRK Ablation Profiles of In Vitro Bovine Eyes and In Vivo Human Eyes Using Indentical Treatments"; Invest Ophthal & Vis Sci; vol. 38, No. 4; p s 534 Mar. 15, 1997.*

* cited by examiner

Primary Examiner—David M. Shay
(74) Attorney, Agent, or Firm—Townsend and Townsend and Crew LLP

(57) ABSTRACT

Systems, methods and apparatus for generating images of portions of the patient's eye, such as the anterior surface of the cornea. The methods and apparatus of the present invention are particularly useful for directly imaging the profile of the ablated region of the cornea during or immediately following a laser ablation procedure, such as photorefractive keratometry (PRK), phototherapeutic keratectomy (PTK), laser in-situ keratomileusis (LASIK) or the like. These methods and apparatus allow the surgeon to precisely image the exterior edge of the eye to characterize the profile of ablated corneas and to determine the spatial variance of tissue ablation rates during the surgical procedures. Methods and apparatus are also provided for generating one or more images depicting the profile of the ablated region of the cornea. The profile is registered with a pre-ablation profile to provide feedback regarding the true ablation properties of the eye. This feedback permits the laser system to be programmed with a laser ablation algorithm based on the measured ablation properties of the eye.

18 Claims, 17 Drawing Sheets

SYSTEMS AND METHODS FOR IMAGING CORNEAL PROFILES

CROSS-REFERENCES TO RELATED APPLICATIONS

This application is a divisional of, and claims priority from, U.S. patent application Ser. No. 09/083,773, filed May 22, 1998, which is a continuation-in-part of, and claims priority from, U.S. patent application Ser. No. 08/863,665, filed May 27, 1997, the full disclosures of which are incorporated herein by reference.

BACKGROUND OF THE INVENTION

The present invention is directed to systems, methods and apparatus for imaging and ablating surface contours. In particular, the invention relates to methods and apparatus for generating direct images of the anterior region of the eye. The present invention is particularly useful for generating silhouette images of the ablated region of the cornea during or immediately following a laser ablation procedure, such as photorefractive keratectomy (PRK), phototherapeutic keratectomy (PTK), laser in-situ keratomileusis (LASIK) or the like. The silhouette images include ablation profiles of the cornea that can be used to refine laser ablation procedures by tailoring the ablation process to match the actual ablation properties of the human eye.

Ultraviolet and infrared laser based systems and methods are known for enabling ophthalmological surgery on the external surface of the cornea in order to correct vision defects. These procedures generally employ an ultraviolet or infrared laser to remove a microscopic layer of an anterior stromal tissue from the cornea to alter its refractive power. In ultraviolet laser ablation procedures, the radiation ablates corneal tissue in a photodecomposition that does not cause thermal damage to adjacent and underlying tissue. Molecules at the irradiated surface are broken into smaller volatile fragments without heating the remaining substrate; the mechanism of the ablation is photochemical, i.e. the direct breaking of intermolecular bonds. The ablation penetrates into the stroma of the cornea to change its contour for various purposes, such as correcting myopia, hyperopia, and astigmatism.

In such laser based systems and methods, the irradiated flux density and exposure time of the cornea to the laser radiation are controlled so as to provide a surface sculpting of the cornea to achieve a desired ultimate surface change in the cornea. To that end, ablation algorithms have been developed that determine the approximate energy density that must be applied to remove a certain depth of tissue from the cornea. At ultraviolet wavelengths, for example, an energy density of 1 joule/cm$^2$ will typically ablate corneal tissue to a depth of about one micron when applied in a series of pulses of about 100 to 400 millijoules/cm2. Accordingly, the ablation algorithms are tailored for each procedure depending on the amount and the shape of corneal tissue removal required to correct the individual refractive error.

Although present laser ablation algorithms are relatively accurate, many of these algorithms assume that tissue ablation is uniformly related to irradiance within the treated zone. Recent studies of corneal topography following PRK, however, have determined that, in some instances, there is a central area of undercorrection called a "central island" for large diameter areas of cornea exposed to a uniform laser irradiance. The term "central island" is generally defined as a central area of corneal ablation that appears to be flattened less than the surrounding ablated area. In contrast to central islands, central overcorrection and peripheral undercorrection within the ablation zone have also been reported following PRK procedures. See e.g., Lin DDTC, et al. *Corneal Topography Following Excimer Photorefractive Keratectomy For Myopia. J. Cataract Refract. Surg.* (1993) 19:149–154. Although mild central topographic changes may not have a large bearing on visual function, some patients with clinically significant central islands can experience visual abnormalities including reduced best corrected visual acuity, monocular diplopia and image ghosting.

Investigators have studied modified ablation algorithms as methods to improve the quality of patient vision and post operative corneal surface. See e.g., Seiler T., et al. *Complications of myopic photorefractive keratectomy with the excimer laser. Ophthalmol.* (1994) 101:153–160. It is believed that some common surface abnormalities (such as central islands) may be at least partially corrected by changing the ablation algorithm. For example, the ablation algorithm may be altered to provide additional laser pulses centrally to offset the effects of central islands.

Currently, the accuracy of modified ablation algorithms is determined from experimental ablation data and post-operative clinical data based on topographic measurement of the healed corneal surface. The healed cornea, however, has been covered by tear films and an epithelium layer with an average thickness of 50 $\mu$. Consequently, topographic measurement of the healed anterior corneal surface after the laser ablation procedure may not accurately portray the true shape of corneal ablations. Accordingly, direct measurement of the ablated corneal surface would be extremely desirable (if not necessary) to understand the effects of changes to laser ablation algorithms on the ablated corneal shape.

Corneal topographic analysis using photokeratoscopic or videokeratographic methods provides objective measures of the quality of the healed anterior corneal surface following ablation procedures, such as PRK, PTK and the like. Current measurement devices, termed videokeratoscopes or corneascopes, typically employ several concentric rings or multiple discrete light sources to reflect a luminous object of known dimension from the cornea. The size of the cornea-reflected images of this object are then measured with photographic or electro-optical recording methods to compare the shape of the cornea with a theoretical spherical shape. If the cornea is spherical, for example, the reflected images of these ring-shaped objects are equally spaced, continuous, concentric ring-shaped patterns. If the cornea has surface defects, or is not precisely spherical, the resultant ring images will be less equally spaced, or they will have a different shape, e.g., elliptical.

One of the drawbacks with many current methods of topographic analysis is that these methods typically treat the cornea as a close approximation to a convex sphere, and they require a specularly reflecting surface. Since the cornea is not precisely spherical, the results of the measurement generally depend on where the non-spherical cornea measurement is taken. Moreover, the corneal surface is not specularly reflective immediately following a laser ablation procedure, such as PRK. Another drawback is that videokeratoscopes do not measure the actual cornea topography, but merely measure the "average" radius. The central few millimeters of the cornea, which is very important optically, cannot be directly evaluated with these devices. Another drawback with these methods is that they are not capable of precisely measuring extremely small surface changes on the anterior corneal surface, e.g., on the order of 20 microns or less. The non-uniform spatial distribution of tissue ablation in laser procedures, however, is generally on the order of about 5–10 microns or less (i.e., about 10–20 percent of the intended ablation depth). Therefore, current methods of topographic analysis are not as accurate for measurements of the spatial variation of tissue removal as one would desire.

It would also be desirable to accurately measure the shape of the ablated region of the cornea during or immediately following the ablation procedure (i.e., prior to healing of the corneal tissue and regrowth of the epithelium layer). This would allow a direct measurement of the ablated surface without the tear films or the epithelium layer interfering with the accuracy of the measurement. In addition, this would allow the surgical team to characterize the profile of ablated corneas and to determine the spatial variance of tissue ablation rates during the surgical procedure, which may afford the opportunity to provide in situ feedback to the surgeon.

Unfortunately, it is extremely difficult to accurately measure the ablated surface of the cornea during or immediately following a surgical procedure with current techniques. One reason for this difficulty is that the epithelium is removed from the cornea prior to PRK to expose the diffusely reflective stromal corneal surface. Thus, keratometry techniques based on reflection are unsuitable. Moreover, although corneal topography utilizing videokeratography can be performed immediately after PRK when artificial tears have been instilled, it is the shape of the tear film and not the ablated cornea which is measured. In addition, the use of corneal topography techniques to assess the acute shape of PRK ablations also suffers from the inability of these instruments to accurately measure surfaces with an abrupt change in curvature.

Projective techniques utilizing rasterstereographic imaging such as the PAR Technologies Corneal Topography System (U.S. Pat. No. 4,995,716) have been used on de-epithelialized and freshly keratectomized corneas. These rasterstereographic systems project a grid on the cornea which is then imaged by a video camera, digitized and analyzed to produce a tabulation of corneal elevations versus corneal diameters. Since the cornea is a transparent member which is non-diffusing to light, however, a grid projected onto the cornea is not sufficiently visible. Thus, a diffusing material, such as talcum powder or a liquid film of fluorescent dye, is typically applied to the cornea to provide a surface on which an image can be visualized. These powders or films degrade the accuracy of the measurement because it is the shape of the powder or film (and not the cornea) that is measured.

What is needed, therefore, are improved methods and apparatus for measuring the outer profile of the eye. In particular, these methods and apparatus should be capable of directly measuring the depth of corneal ablation to the order of about 5.0 to 10.0 Mm or less in order to evaluate the spatial variance of tissue ablation rates. Further, it would be particularly desirable if these methods and apparatus were capable of directly measuring the ablated region of the cornea during or immediately following the laser ablation procedure to provide an accurate profile of the ablated corneal surface (without adding a liquid film or powder to this surface). Such information may be used to modify the ablation algorithm based on differences between the theoretical and directly measured ablation profiles.

SUMMARY OF THE INVENTION

The present invention is directed to systems, methods and apparatus for generating images of the eye, such as the anterior surface of the cornea. The methods and apparatus of the present invention are particularly useful for directly imaging the profile of the ablated region of the cornea during or immediately following a laser ablation procedure, such as photorefractive keratometry (PRK), phototherapeutic keratectomy (PTK), laser in-situ keratomileusis (LASIK) or the like. These methods and apparatus allow the surgeon to precisely image the exterior edge of the eye to characterize the profile of ablated corneas and to determine the spatial variance of tissue ablation rates during the surgical procedures. In an exemplary embodiment of the present invention, methods and apparatus are provided for generating one or more images depicting the profile of the ablated region of the cornea. The profile is registered with a pre-ablation profile to provide feedback regarding the ablation properties of the eye. This feedback permits the laser system to be programmed with a laser ablation algorithm based on the measured ablation properties of the eye.

In one aspect of the invention, a method is provided that includes projecting light against a surface adjacent to or near the eye and reflecting the light from the surface across an anterior region of the eye. A portion of the reflected light is received by a photodetector, such as a charge coupled device (CCD), and the corresponding signals are processed to generate a high contrast silhouette image of the anterior region of the eye. The silhouette image includes a dark portion representing the light that is occluded by the cornea and a light portion representing the light that passes across the eye. The light and dark portions define a high contrast line therebetween that represents the profile of the cornea. Providing a direct, silhouette image of the front edge of the eye improves the resolution as compared to previous methods that approximate the corneal profile based on measuring reflected light patterns. For example, the silhouette image generated by the present invention has sufficient data points to minimize smoothing or approximation of the line, which provides a high resolution profile of the anterior surface of the cornea. In addition, the method of the present invention allows a direct image of the eye to be generated without applying a substance to the corneal surface, which improves the accuracy of the measurement.

In a specific embodiment, the projected light is reflected directly off the lateral surface of the patient's nose, or a reflector positioned between the eye and the lateral surface of the patients nose. The light is directed against this surface at an angle selected so that the light will reflect back across the front portion of the eye to "back illuminate" the eye. This method overcomes the potential problem that the nose could interfere with the transmission of light obliquely across the eye. In addition, it allows the eye to be measured while minimizing the amount of light that passes directly into the eye, and without positioning the optics directly in front of the eye. Preferably, a light pattern having a partially annular shape is projected against a diffuse reflector, such as baked enamel or white material attached to the patient's nose. This partially annular shape is similar to a crescent shape except that the ends of the inventive shape do not taper to a point as in a crescent. The partially annular shaped light pattern reduces light scattering at the edge of the profile to increase the contrast and improve the resolution of the image.

The silhouette image will typically comprise a single meridian or plane of the eye, taken from a non-parallel angle relative to the optical axis of the eye (preferably perpendicular or substantially perpendicular to the optical axis of the eye). To accurately image the entire outer profile of the cornea, a plurality of silhouette images of different meridians are generated, and then combined together to form a two or three dimensional image of the eye. These separate images may be created by moving the eye to different positions, and imaging the eye at each position, or by moving the optics such that each image is generated from a different angle relative to the optical axis.

In another aspect of the invention, systems and methods are provided for generating a direct image of the ablated corneal surface of the eye during or immediately following a surgical procedure, such as photorefractive keratectomy (PRK), phototherapeutic keratectomy (PTK), laser in-situ keratomileusis (LASIK) or the like. During the laser ablation procedure for PRK, the epithelium is removed to expose the underlying Boyman's layer of the cornea. In LASIK procedures, the epithelium, Bowman's membrane and a portion of the anterior stroma are partially incised from the stroma and folded back to expose the stroma to the laser. An ultraviolet or infrared laser is employed to remove a microscopic layer of anterior stromal tissue from the cornea to alter its refractive power.

According to another aspect of the present invention, one or more direct images are generated of the ablation profile of the cornea. The direct images are then registered with one or more pre-ablation profiles of the cornea to characterize the profile of ablated corneas and to determine the spatial variance of tissue ablation rates during surgical procedures. This information is then used to generate a laser treatment based on the actual properties of the eye to increase the precision of future laser ablation procedures. Alternatively, this information may be used in situ to alter the ablation algorithm during the procedure to compensate for spatial variations along the ablation profile. In some embodiments, a number of ablation subtreatments are performed on the cornea, with each subtreatment having a shape and a depth selected so that the overall laser treatment ablates a desired shape and depth in the cornea. A direct image is generated of the ablation profile of each these subtreatments to calculate the laser treatment. In an exemplary embodiment, each subtreatment further comprises a plurality of laser pulses that combine to form the subtreatment. In this embodiment, a direct image is generated of the abated profile after each laser pulse so that the corneal profile of each laser pulse can be calculated to determine the overall laser treatment.

In one embodiment, direct images of a plurality of ablation profiles from different human eyes are generated, and a laser treatment is calculated based on an average ablation profile representing ablation characteristics of an average human eye. In another embodiment, the laser treatment for an individual eye is calculated based on one or more ablation profiles of that particular individual eye. The cornea is then subjected to another ablation treatment based on the newly calculated laser treatment for that particular eye. In yet another embodiment, the invention provides a method for generating a direct image of a plurality of ablation profiles with the same laser, and calculating the laser treatment based on ablation characteristics of that particular laser.

DESCRIPTION OF THE SPECIFIC EMBODIMENTS

Figure 1:
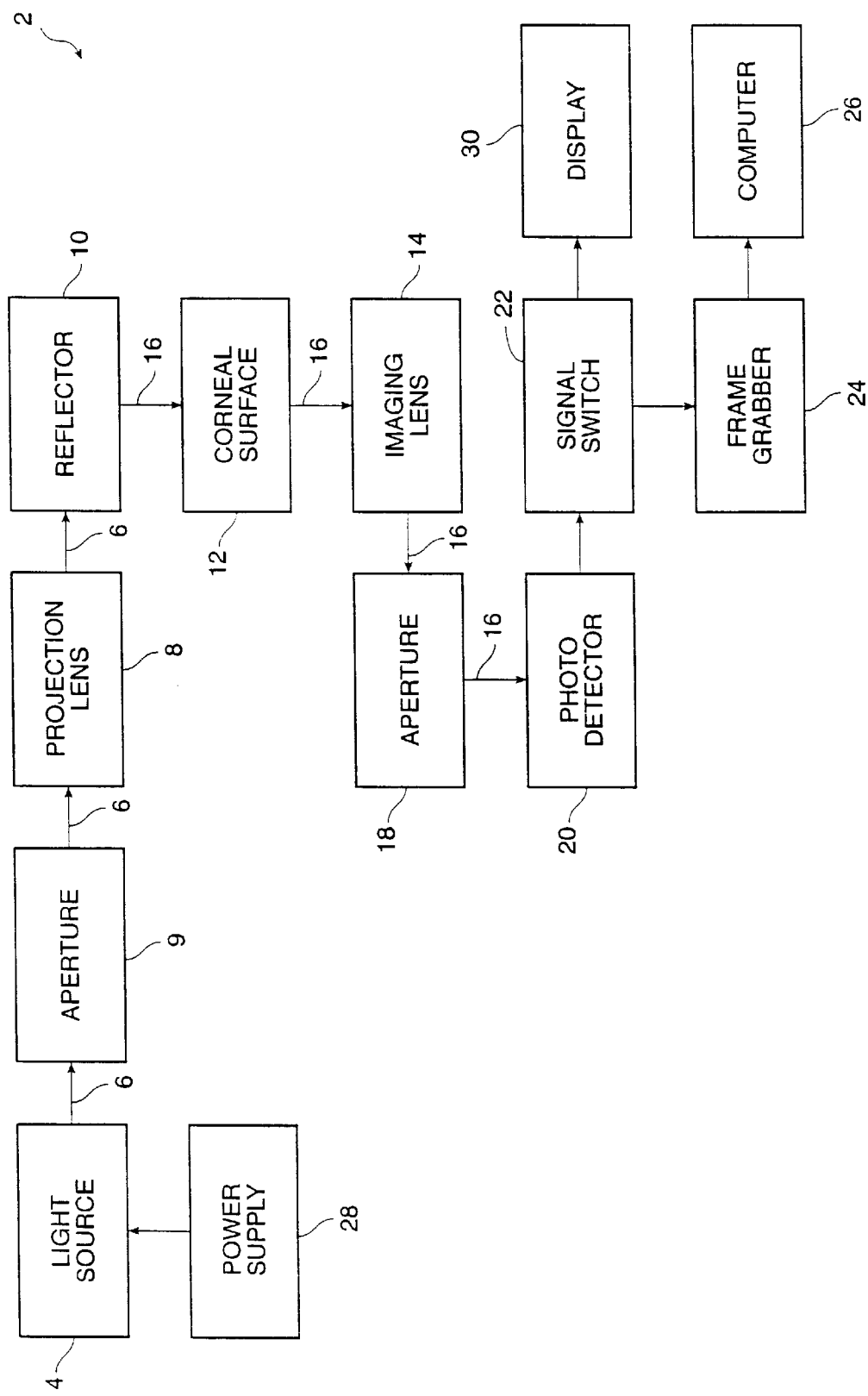
FIG. 1 is a simplified block diagram illustrating the functional relationships of generalized optical mechanical and electrical components of an optical system of the present invention.

The present invention is directed to systems, methods and apparatus for generating profiles of anterior regions of the patient's eye, such as the anterior surface of the cornea. The present invention is particularly useful for imaging the anterior surface of the optically useful region of the cornea. For convenience, the remaining disclosure will be directed specifically to systems and methods for generating profiles of the region of the cornea underlying the epithelium, often referred to as Bowman's layer and/or the anterior surface of the stroma (as well as the non-removed portions of the epithelium). Bowman's layer and the stroma are layers that can accommodate permanent change in the contour of the cornea. However, it will be appreciated that the system and method can be applied equally well to procedures involving other tissue structures within the eye, such as the epithelium or other regions of the cornea.

The present invention employs a light projecting assembly to project light against a reflector such that the reflected light passes across the anterior region of the eye, and an image generating assembly to receive the light and generate a direct, silhouette image of this anterior region. The silhouette image created by the present invention will typically comprise a two dimensional representation of the outline or profile of the anterior region of the cornea. The outline may be suitably processed such that the cornea is depicted by a darker region outlined against a lighter background to provide a sharp contrast at the edge of the cornea. The silhouette image will typically comprise a single meridian or plane of the eye, taken from a non-parallel angle relative to the optical axis of the eye. Usually, the light is reflected across the eye at an angle of about 70–110 degrees relative to the optical axis of the eye, and preferably the light passes across the eye substantially perpendicular to this axis. To accurately image the entire outer profile of the cornea, a plurality of silhouette images of different meridians are generated, and then combined together to form a two or three dimensional profile of the eye. These separate images may be created by allowing the patient to move/rotate the eye into different known positions, and imaging the eye at each position. These positions may be established, for example, by having the patient sequentially look at discrete light sources positioned at different angles relative to the optical axis of the system. Alternatively, the eye may be held in a fixed position and the optics may be moved such that each image is generated from a different angle relative to the optical axis.

Providing a direct, silhouette image of the front edge of the cornea improves the resolution as compared to previous methods that approximate the corneal profile based on measuring reflected light patterns. For example, the silhouette image generated by the present invention has sufficient data points to minimize smoothing or approximation of the curve at the anterior surface of the cornea, which provides a high resolution profile of this surface. Usually, the image will accurately portray surface contour changes on the order of less than 20 microns, preferably less than 10 microns, and more preferably less than 3 microns.

In addition, the method of the present invention allows a direct profile of the eye to be generating without applying a substance to the corneal surface. By contrast, rasterstereographic systems that project a grid on the cornea which is then imaged by a video camera require the application of talcum powder or a liquid film to the corneal surface in order to visualize this surface. In these systems, the liquid film or talcum powder is measured rather than the cornea.

The light is reflected in such a manner that it will pass over the anterior region of the eye, preferably at an angle that minimizes the amount of light scattering from the corneal surface: In one embodiment, the light is reflected directly off the lateral surface of the patient's nose, or a reflector positioned between the eye and the lateral surface of the patient's nose. In alternative embodiments, the light is projected directly across the eye into a photodetector, or into a mirror that reflects the light into a photodetector remote from the eye. For example, this may be accomplished by positioning a light source, aperture and projection lens to project collimated light across the eye to infinity. The light will pass across the anterior region of the eye at an angle that will minimize the amount of light scattering from the corneal surface and interfering with the generated image. In addition, an aperture is preferably provided between the reflector and the light detector to inhibit non-parallel light from passing through the aperture to the detector. This additionally minimizes or prevents light scattering from the corneal surface that may interfere with the image.

The methods and apparatus of the present invention are particularly useful for imaging the profile of the ablated region of the cornea during or immediately following a laser ablation procedure, such as photorefractive keratometry (PRK), phototherapeutic keratectomy (PTK), laser in situ keratomileusis (LASIK) or the like. These methods and apparatus allow the surgeon to precisely image the exterior edge of the eye to characterize the profile of ablated corneas and to determine the spatial variance of tissue ablation rates during the surgical procedures. Accordingly, the silhouette images are preferably generated immediately following the ablation of the cornea before the cornea heals, and before the epithelium regrows (i.e., PRK and PTK procedures), or before it is reattached to the cornea (LASIK procedures). These images may be created after the ablation procedure has been completed, or they may be created during the procedure, e.g., between laser pulses to capture the ablation profile of each pulse. In the former case, the profiles may be used to provide feedback regarding the ablation properties of the eye. This feedback may then be used to further tailor or modify the ablation algorithm, and to program the modified ablation algorithm into the laser system prior to subsequent treatments. In the latter case, this feedback may be used in situ to alter the ablation algorithm during the surgical procedure.

Referring to FIG. 1, an optical system 2 for generating images of anterior portions of the eye is schematically illustrated according to the present invention. Optical system 2 includes a light source 4 for directing a single or a plurality of light rays 6 through an aperture 9 and a projection lens 8 onto a reflector 10. The light rays 6 are reflected from reflector 10 across the exterior surface of the cornea 12 into an imaging lens 14. Imaging lens 14 focuses the reflected light 16 through an aperture 18 and onto a photodetector 20 to form the measurable optical images. A signal switch 22, a frame grabber 24, and a computer 26 are in electrical communication with the photodetector 20 for digitizing the video images and processing these images with, e.g. an edge detection program, for determining the corneal profile.

The light source 4 is activated by a power supply 28 to pass light rays 6 through aperture 9 and projection lens 8 and aperture 9, which preferably images aperture 9 onto reflector 10. The light source 4 may comprise one or more light sources, e.g., lasers such as argon, helium-neon, diode, dye, or other light sources, such as halogen light sources, light emitting diodes, fiberoptics, and the like. In one embodiment, the light source will emit light having a red to near infrared wavelength, about 700–900 nanometers. This wavelength range has the highest sensitivity for many detectors, and it also allows the optics to filter light from other sources, such as an ultraviolet or infrared laser, a microscope viewing light or the light from the operating room (which is typically in the 400 to 700 nanometer range). The light source may be configured to directly emit such wavelengths, e.g., filtered halogen light sources that only transmit wavelengths within the red to near infrared range.

Figure 6:
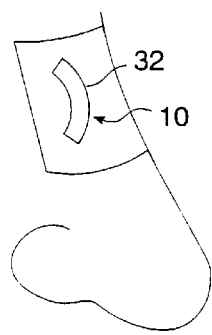
FIG. 6 is an enlarged view of a reflector of the optical system of FIG. 1, illustrating a partial annular shape that is projected onto the reflector in one embodiment of the present invention.

Projection lens 8 is preferably constructed such that it will image the aperture 9 onto reflector 10. As discussed below, lens 8 will typically be positioned to the side of the patient's head, and reflector 10 will typically be positioned between the cornea and the patient's nose (see FIGS. 4 and 5). Therefore, the focal length of lens 8 will depend on the preferred position of the optics relative to the patient. Aperture 9 comprises an opening having a partially annular shape that is approximately the same shape as the anterior surface of the cornea (see FIG. 6). The partially annular shape of the opening will preferably be similar to a crescent shape without the tapered points at either end. The opening will be shaped to allow a partially annular shaped light pattern therethrough having a width sufficient to illuminate the exterior portion of the eye. Usually, the projected aperture will have a width of about 6 to 12 mm, and preferably about 8 to 10 mm. The partially annular shaped light pattern improves the resolution of the line or curve between the dark and light regions of the image. Since the eye appears as a dark object with a light background, light which scatters from the surface of the eye and is imaged onto the detector can make the upper edge of the eye appear light rather than dark. Illuminating the eye from behind can minimize this decreased contrast. This illumination minimizes the amount of light which strikes the front surface of the eye as seen by the detector, thereby increasing image contrast and profile resolution. The above illumination can be accomplished by projecting collimated light over the eye, or by projecting a partial annulus sufficiently far behind the eye such that the light rays passing over the eye and into the imaging lens are nearly collimated. Because of this illumination, relatively few light rays will illuminate the front surface of the portion of the eye seen by the detector. An annulus is a preferred geometry to project onto a diffusing surface behind the eye because it will minimize the amount of scattered light striking the front surface of the eye as seen by the detector.

The reflector 10 may comprise any diffuse surface that minimizes non-uniform light scattering, such as white tape attached to the patient's nose, baked enamel attached to a speculum behind the eye or the like. Of course, light may be reflected directly off the patient's nose. Since the nose is not a uniformly scattering surface, however, a reflector 10 having a uniformly scattering surface is preferable. The reflector 10 is positioned relative to the light source 4 and the projection lens 8 such that scattered light is occluded by the front surface of the eye prior to imaging lens 14. This projection system overcomes the potential problem that the nose could interfere with the transmission of light across the eye. In addition, it allows the eye to be measured while minimizing the amount of light that passes directly into the eye, and without requiring that the optics be positioned directly in front of the eye.

In an alternative embodiment, reflector 10 may comprise a mirror (not shown) that is suitably designed and positioned to reflect light obliquely across the eye to photodetector 20. In this embodiment, projection lens 8 is configured to project collimated light into the mirror and across the eye. The mirror serves to reflect collimated light across the eye and onto photodetector. In yet another alternative, light source 4, aperture 9 and lens 8 may be positioned to project light directly over the eye. In this embodiment, the light source may comprise one or more light emitting diodes (e.g., arranged in a crescent or partially annular array) that project light across the eye into the photodetector, which processes the light signals to generate the image.

The reflected light rays 16 pass through imaging lens 14, which focuses the rays through an aperture 18 and forms an image of the eye on the photosensitive surface of the photodetector 20. In an exemplary embodiment, imaging lens 14 is configured to minimize distortion and aberration across the image. Further, imaging lens 14 may comprise a telecentric lens to maintain constant magnification with increased depth of field. In preferred aspects, the invention may further employ autofocus systems to focus both the projected light 6 onto reflector 10 and the reflected light 16 onto photodetector 20.

Aperture 18 will usually have a diameter of about 1 mm, and is preferably positioned at the focal length of the imaging lens 14 to provide improved depth of field and to remove spurious light which will degrade the contrast at the edge of the eye. Aperture 18 effectively ensures that only light travelling parallel or near parallel to the optic axis of lens 14 will pass through aperture 18. In addition, filters such as dichroic mirrors or beam splitters may be included in the optical train to filter spurious light. These filters are transmissive to radiation at the wavelength of the light source while reflective to radiation at other wavelengths thus effectively separating the light rays 6 projected onto reflector 10 from other light sources in the operation room.

Electrical output signals generated by photodetector 20 are directed by signal switch 22 to a frame grabber 24 which produces a time sequence series of electrical signals representative of the spatial distribution of energy and the image formed by lens 14. These electrical signals can be displayed as a real-time video image in a display apparatus 30. Alternatively or in addition, the electrical signals can be stored in digital form by a frame grabber 24 for further analysis by a computer 26 and/or for supply to display apparatus 30. Computer 26 will include a processor and appropriate software, such as an edge detection program for determining the edge of the eye to increase the resolution of the corneal profile. Special algorithms may also be stored in computer 26 for computation of the corneal profile, registration of the ablated profile with a pre-ablated profile of the cornea, etc. Some of these algorithms are discussed in more detail below.

Photodetector 20 may comprise a conventional photodetecting device having photocathodes and a video contact image. Alternatively, photodetector 20 may comprise an array of discrete detectors such as a charge coupled device (CCD) Typically, the detector would comprise a CCD array with usable aperture dimensions of about 6.6 by 8.7 mm and would be sensitive to the light emitted by light source 4. Selecting an appropriate number of resolution elements for the detector array can vary the resolution of the system. For example, to obtain a desired resolution of 3 $\mu$m, the imaging system would be configured so as to provide at least 1 pixel per 6 $\mu$m of elevation on the eye. By interpolating between pixel elements, resolution of 3 $\mu$m may be obtained. Many suitable detectors are commercially available such as the Electrim EDC 1000U (Electrim Corporation, Princeton, N.J.) which provides an array of 972 by 1134 detector elements. With this camera, a 5.8 mm portion of an eye imaged to 6.6 mm at the detector will provide one pixel for each 6 $\mu$m of elevation of an eye. If desired, detectors with a substantially greater number of elements may be utilized.

Figure 2:
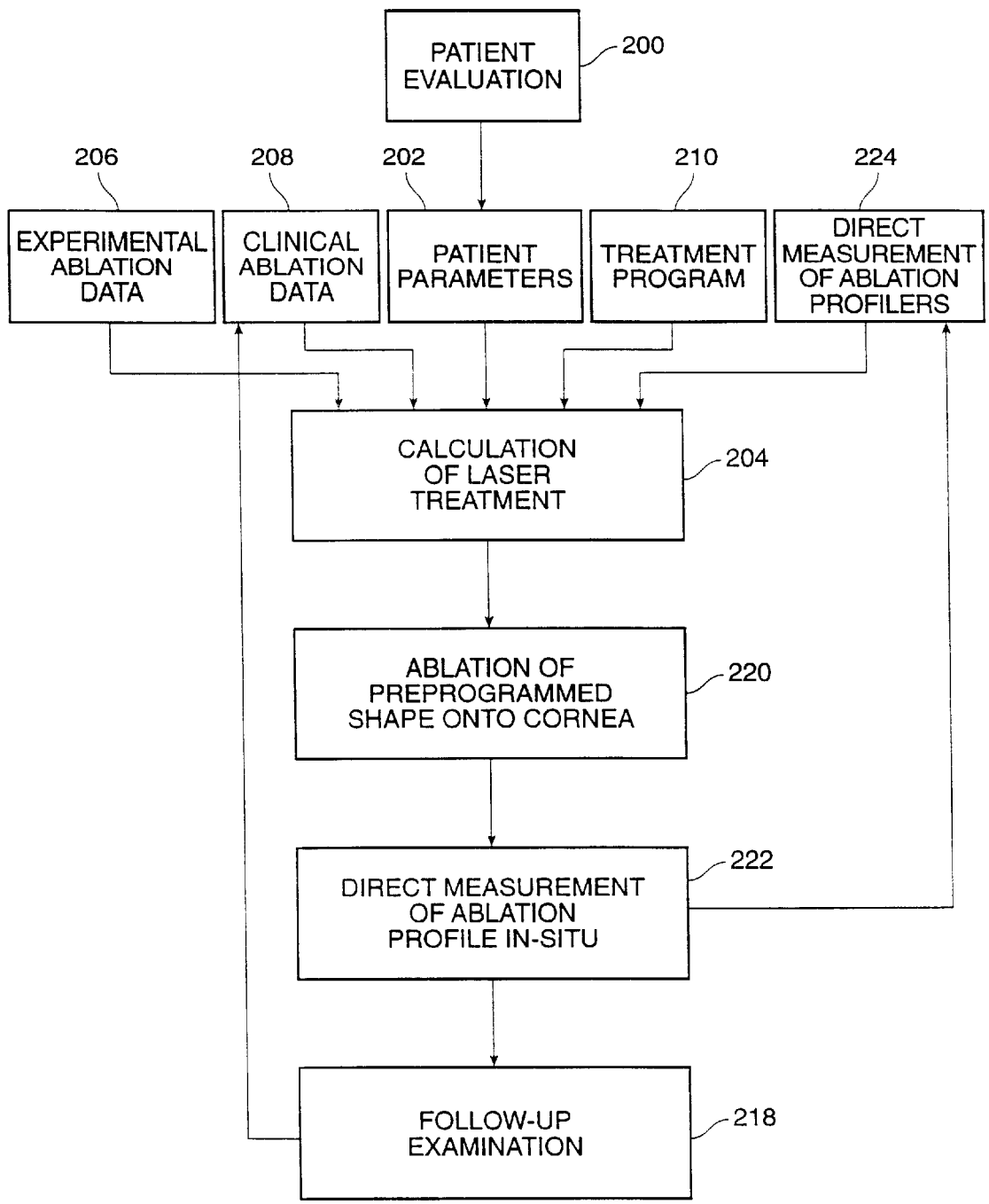
FIGS. 2 and 3 are flow charts illustrating the steps for calculating a laser treatment algorithm for ablating a desired shape onto the cornea according to the present invention.

Referring to FIG. 2, a method for calculating a laser treatment algorithm for ablating a desired shape onto the cornea will now be described. The physician conducts an initial patient evaluation 200 to determine whether the patient's cornea is suitable for a laser ablation procedure and to determine the refractive error that will be corrected, e.g., myopia, hyperopia, hyperopic astigmatism, myopic astigmatism, mixed astigmatism or the like. After this evaluation is completed, patient parameter information 202 will be collected. For example, the nature and size of the refractive error will be determined to calculate the desired ablation shape that will be applied to the patient's cornea. This information may be obtained from the patient's eyeglass or contact prescription, or a measurement of the curvature and refractive power of the patient's cornea through corneal topographic analysis (e.g., keratometry, photokeratoscopy and/or videokeratography). The information regarding patient parameters is then used to prepare one or more ablation algorithm(s) or a laser treatment 204 for ablating a desired corrective shape onto the cornea.

In addition to patient parameter information 202, experimental ablation data 206 may also be used in the calculation of the laser treatment algorithms(s) 204. This experimental ablation data 206 includes, among other things, the spatial and temporal distribution of laser pulses required to ablate the desired corrective shape onto the cornea. The ablation algorithm may also be modified based on post-operative clinical ablation data 208. The clinical data 208 is typically obtained during a follow up examination 218 of the patient after a laser ablation procedure has been completed. This clinical data 208 may, for example, include differences between the theoretical and measured ablation profiles, such as central islands.

Figure 3:
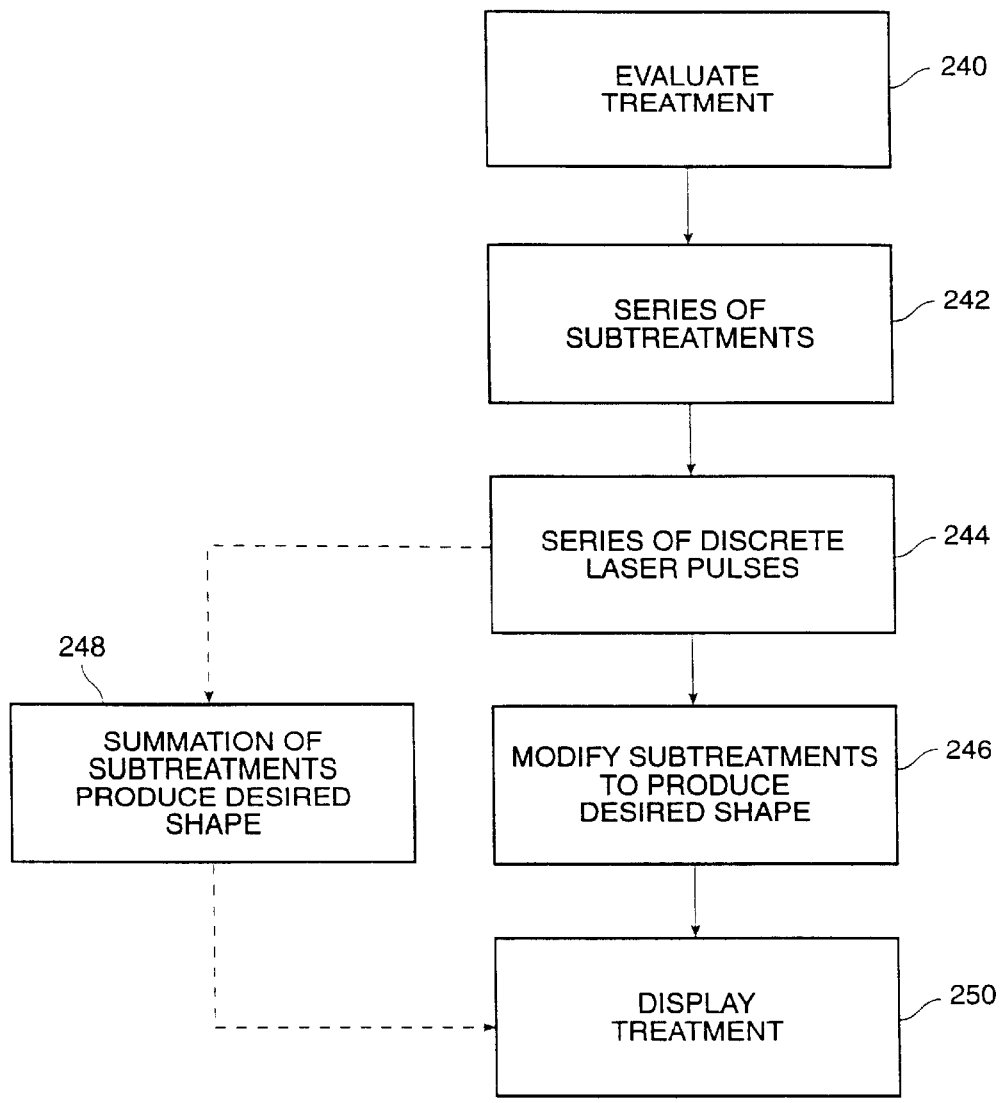

In addition, a treatment program 210 for ablating the desired shape onto the cornea based on the above factors will be determined for the particular operation. FIG. 3 is a flow diagram of an exemplary treatment program 210, but it will be recognized that a variety of other treatment programs may be employed. As shown, the laser treatment for the particular patient is evaluated 240 and divided into a series of subtreatments 242. For example, if a −6D ablation is desired, the laser may be programmed to ablate a series of −1D ablations. These subtreatments are then further broken down into a series of discrete laser pulses 244 in which the laser is configured to a desired state prior to each pulse. To produce the desired shape on the cornea, the subtreatments 242 may then be individually modified 246, or the summation of subtreatments 248 may be designed to produce the desired shape. Finally, desired treatment is displayed on a video display 250 or similar display apparatus.

Referring again to FIG. 2, after the laser treatment has been calculated, a preprogrammed shape is ablated onto the patient's cornea at step 220. During or immediately following this ablation, the ablated corneal profile is directly measured at step 222 as discussed below in reference to FIGS. 4 and 5. This measurement will provide a corneal ablation profile that allows measurement of the spatial variation of tissue ablation with laser irradiance for an actual eye. This measurement is then used as feedback 224 to modify the ablation algorithm for the laser treatment in future procedures. Typically, measurements will be conducted for a number of different procedures and then normalized to determine an ablation profile for the "average" eye. This normalized ablation profile is used to provide a more accurate laser treatment program. Alternatively, the feedback 224 may be employed in situ to modify the ablation algorithm, modulate the laser beam, etc., such that the actual ablation profile closely approximates the desired profile.

The measurements of the corneal ablation profile may be taken after the entire treatment has been conducted, between subtreatments and/or between each discrete laser pulse. In the latter cases, a number of laser treatments may be custom generated based on the ablation profiles of each subtreatment and/or laser pulse in the procedures. For example, if a −10D ablation is desired, the laser may be programmed to ablate a series of −1D ablations or subtreatments, with a measurement taken between each −1D ablation. Each measurement is then registered with the pre-ablation profile to determine an actual shape and depth of each subtreatment.

The laser treatment is calculated by generating a pre-ablation profile of the cornea, storing this pre-ablation profile in a memory and registering the ablated profile with the pre-ablation profile to determine a spatial variation of tissue ablation on said region of the cornea. In a preferred embodiment, the pre-ablation profile is larger than the selected ablation region so that it include portions of the cornea that are peripheral to the ablated region. The direct image also includes these peripheral regions so that the pre and post ablation profiles can be registered by aligning the peripheral regions of the direct image with the peripheral regions of the pre-ablation profile.

Figure 4:
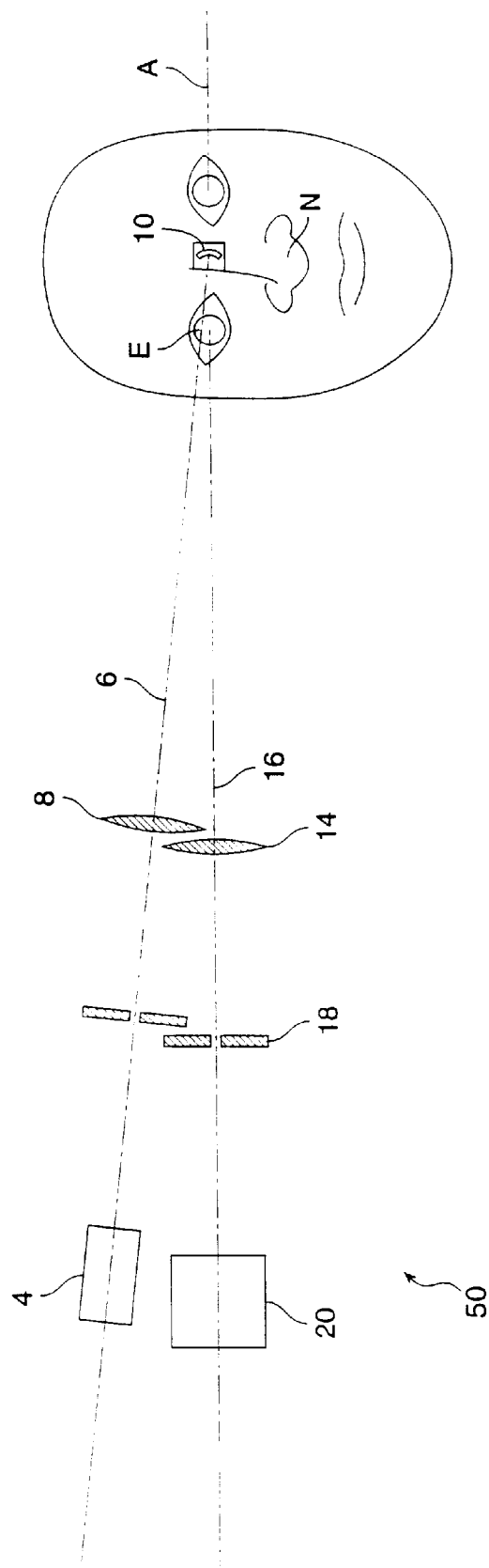
FIGS. 4 and 5 are front and isometric schematic views, respectively, of the optical system of FIG. 1, illustrating a method of generating silhouette images of the anterior region of the eye according to the present invention.
Figure 5:
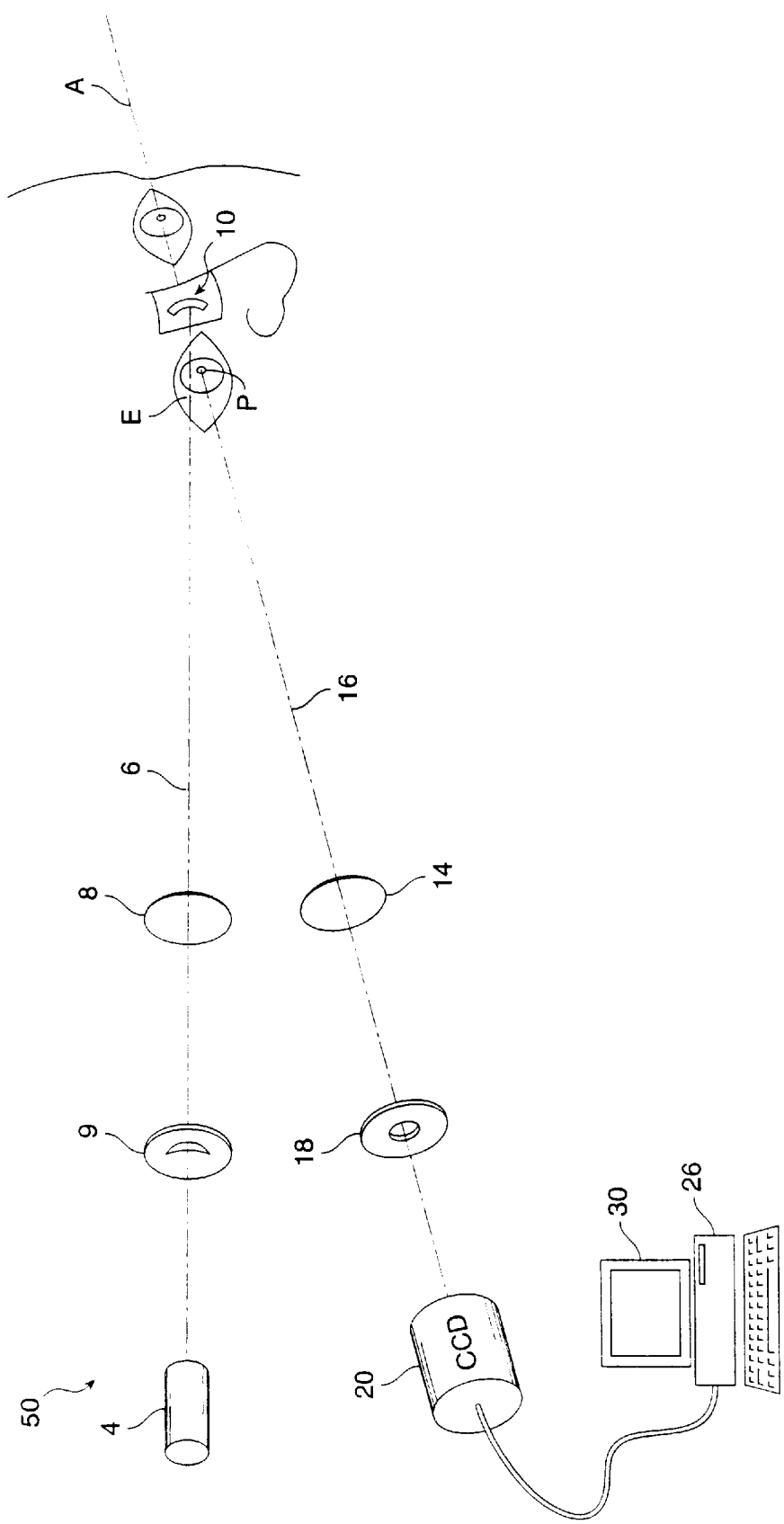

Referring to FIGS. 4 and 5, an exemplary optical system 50 is illustrated and described in use for generating images of the anterior region of a patient's eye E. As shown, optical system 50 is preferably disposed toward the side of the patient's head to project light across the patient's eye to minimize scattered light, which could interfere with the image. In addition, this configuration minimizes interference with the laser apparatus and/or surgical microscope that will be used during a surgical procedure (see FIG. 9). Projecting light from the side of the patient's head in this manner and generating images without measuring the reflected light from the eye allows the images to be generated intraoperatively. Thus, for example, direct silhouette images may be generated during or immediately following a laser ablation procedure so that a profile of the actual ablated surface of the Bowman's layer or the stroma can be obtained (i.e., without the tear film or the regrown epithelium layer).

The optical system 50 may include a suitable patient station (not shown) of known design used to position the patient's eye at a desired position in three dimensional space. The eye is positioned so that the anterior portion is in focus and centered on the image detector. The imaging system is aligned with the laser so that the eye is positioned properly for both laser treatment and profilometry. This alignment permits measurements of the eye during surgery without requiring that the treatment be interrupted to align the eye with the profilometer.

As shown in FIGS. 4 and 5, light from light source 4 is projected through aperture 9 and lens 8 such that it strikes reflector 10 on the patient's nose. Preferably, the light will strike at an acute angle relative to the horizontal eye axis A at a point behind the eye such that the reflected light 16 passes across the eye generally parallel to axis A. Since the distance between the lateral surface of the nose and the cornea will vary for different individuals, light source 4, aperture 9 and lens 8 will be vertically movable relative to reflector 10. Preferably, the angle between the projected light 6 and the reflected light 16 will be substantially constant (usually about 1 to 10°) regardless of this distance. Accordingly, light source 4, aperture 9 and/or lens 8 will be adjusted vertically relative to horizontal axis A such that the aperture 9 imaged onto reflector 10 is reflected directly across the target region of the cornea. Light source 4 may be moved manually, or with suitable drive motors that may be controlled by computer 26.

The reflected light 16 passes over the anterior region of the cornea to imaging lens 14, where a portion of the light 16 is occluded by the cornea, as discussed above. The parallel light is then focused through aperture 18 and imaged onto photodetector 20. Reflected light rays which are not substantially collimated are occluded by aperture 18. The image is processed with frame grabber 24 and computer 26. The projected light 6 will preferably have a partially annular shape that substantially corresponds with the outer contour of the cornea, and having a width sufficient to create a two-dimensional silhouette image that extends on either side of the exterior surface of the cornea. This typically creates a high contrast image of a single meridian of the cornea. The high contrast image includes a line or curve that represents the outer edge or profile of the cornea. Usually, this line will accurately portray surface contour changes on the order of less than 20 microns, preferably less than 10 microns, and more preferably less than 3 microns.

Figure 7:
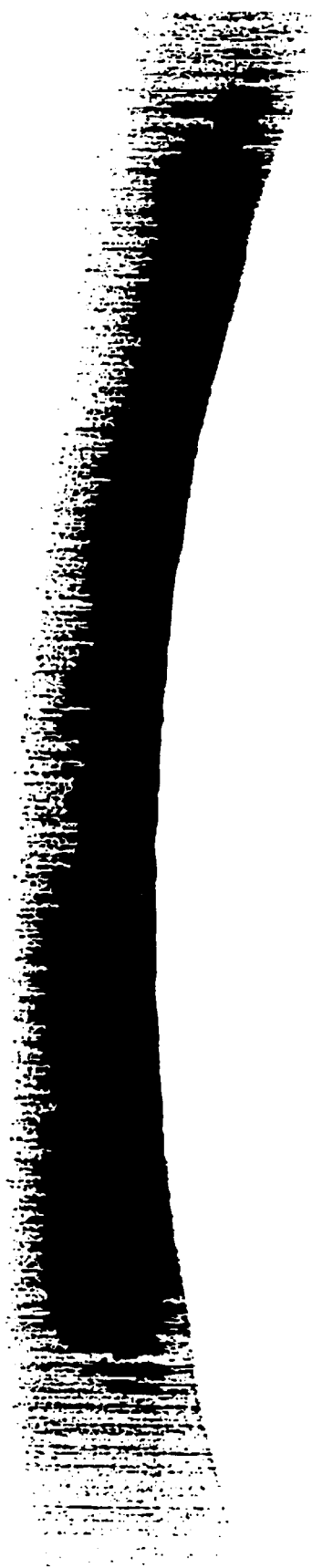
FIG. 7 illustrates an image of the ablated corneal surface of a human eye generated by an optical system and method of the present invention.

By ensuring that the eye is properly aligned, the generated image allows the precise measurement of the distance between a reference point and the exterior surface of the cornea. Thus, by registering this image with, e.g, a pre-ablation profile of the cornea, the ablation profile may be calculated. To that end, the light rays 6 projected onto reflector 10 will typically be sized so that they pass over the entire ablation region, and onto a portion of the non-ablated region of the cornea (either above and below the ablated region, or on either side of this region). The profile of the non-ablated region of the cornea can be used to register the post-ablation profile with the pre-ablation profile. An example of a silhouette image of a human eye generated according to the systems and methods of the present invention is illustrated in FIG. 7.

Figure 9:
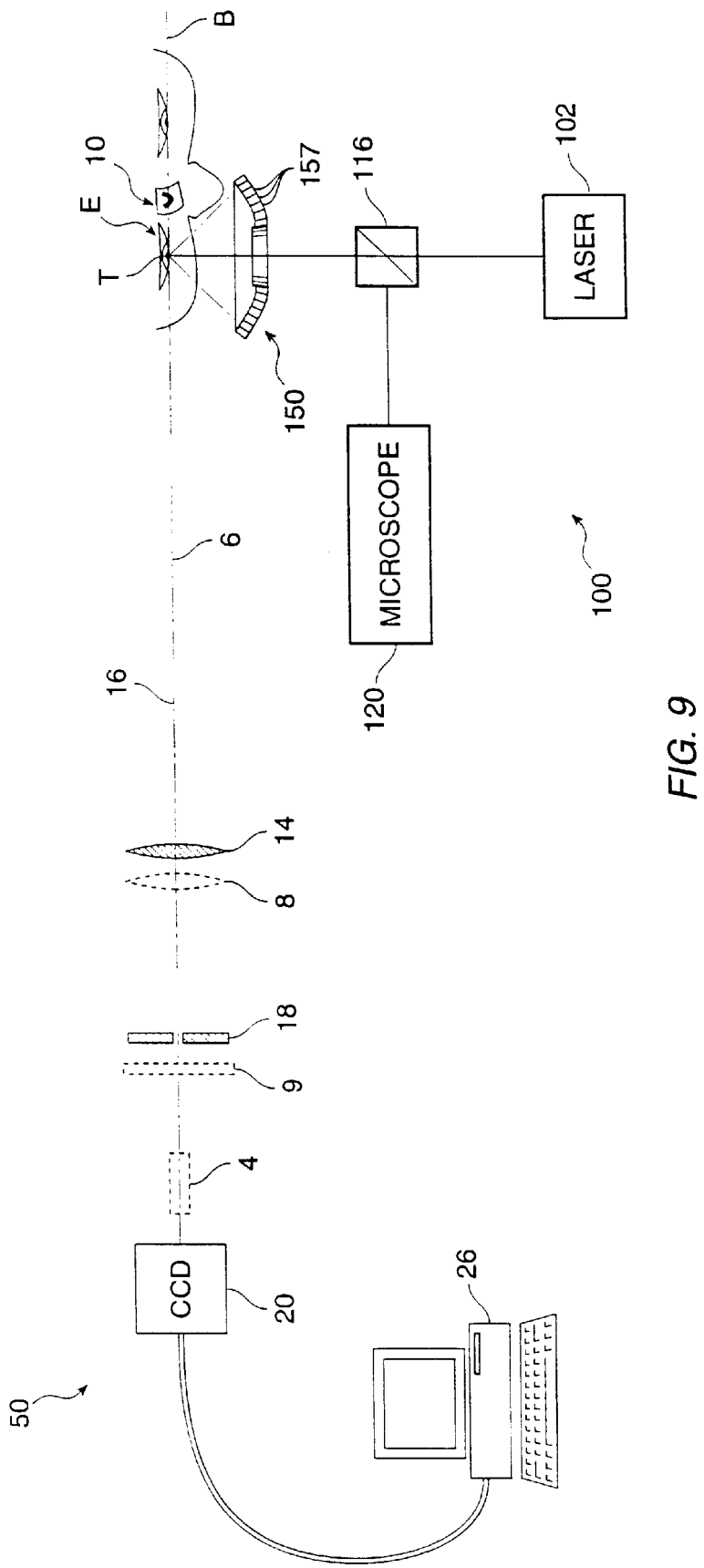
FIG. 9 schematically illustrates a method for generating images of the ablated corneal surface during a laser ablation prodedure.
Figure 10:
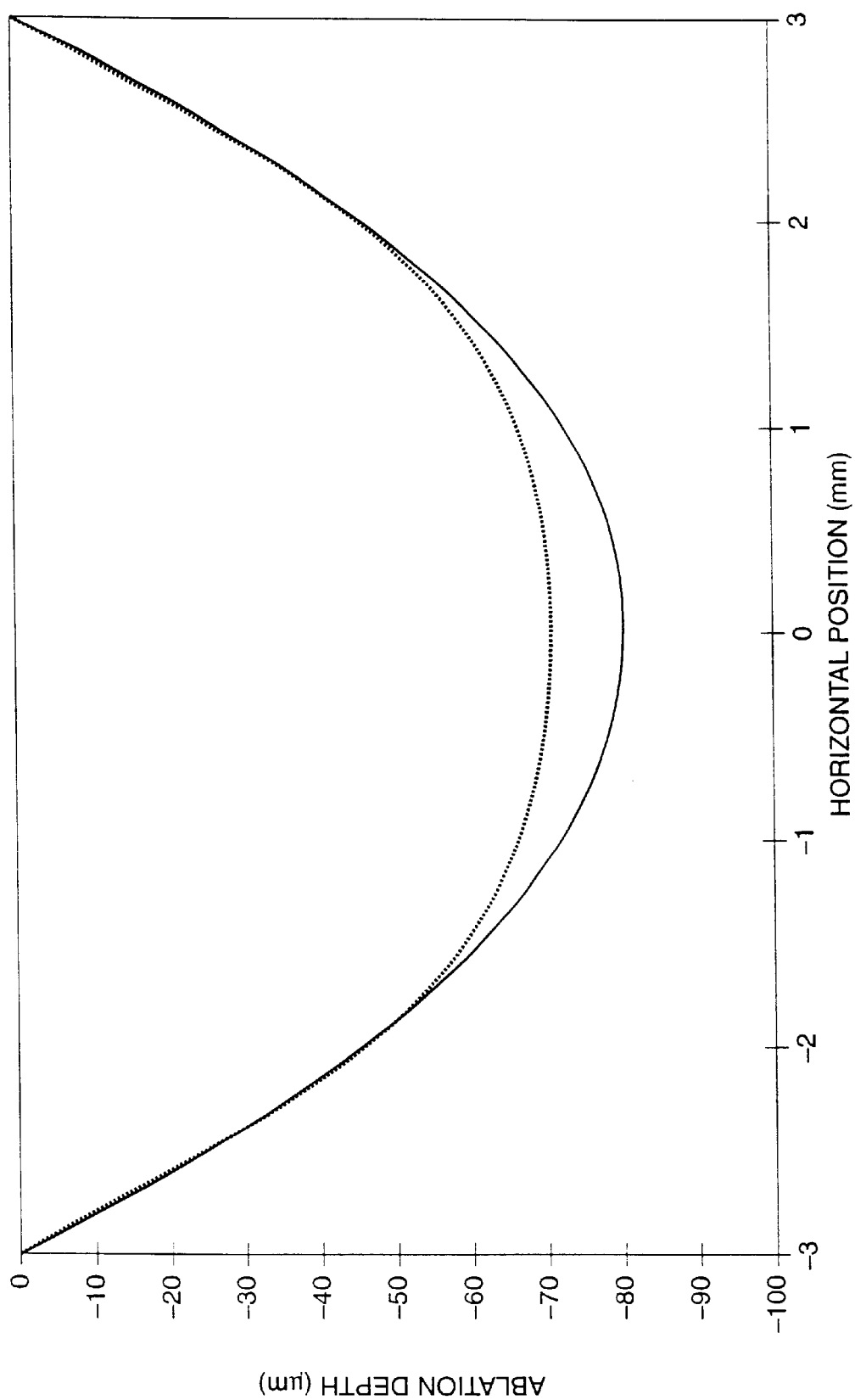
FIG. 10 illustrates a theoretical profile of ablation depth versus position with (dashed line) and without (solid line) a central island.
Figure 11:
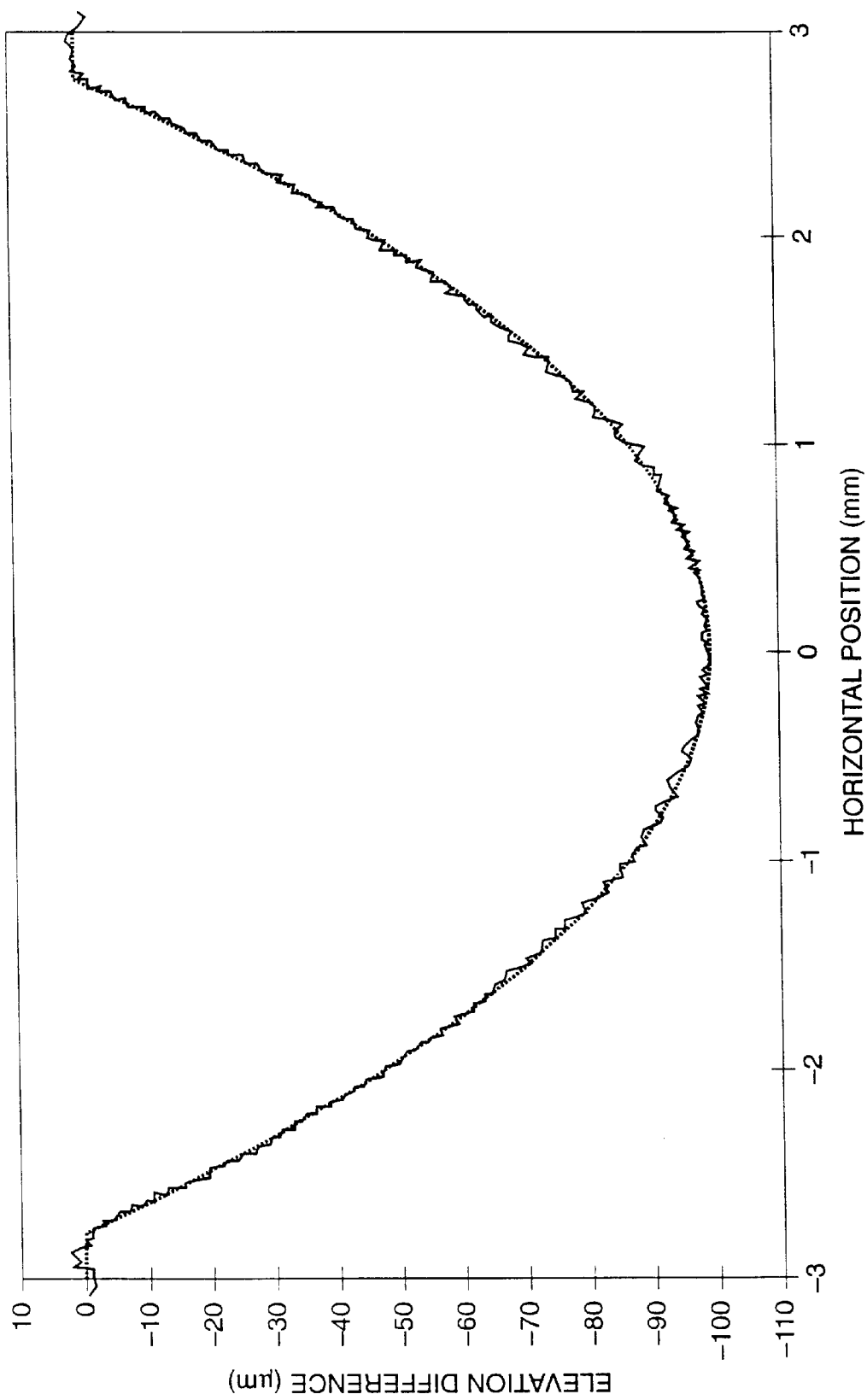
FIG. 11 illustrates an ablation similar to that of FIG. 10 in which the ablation algorithm has been modified using feedback from the corneal profiles of the present invention.
Figure 12A:
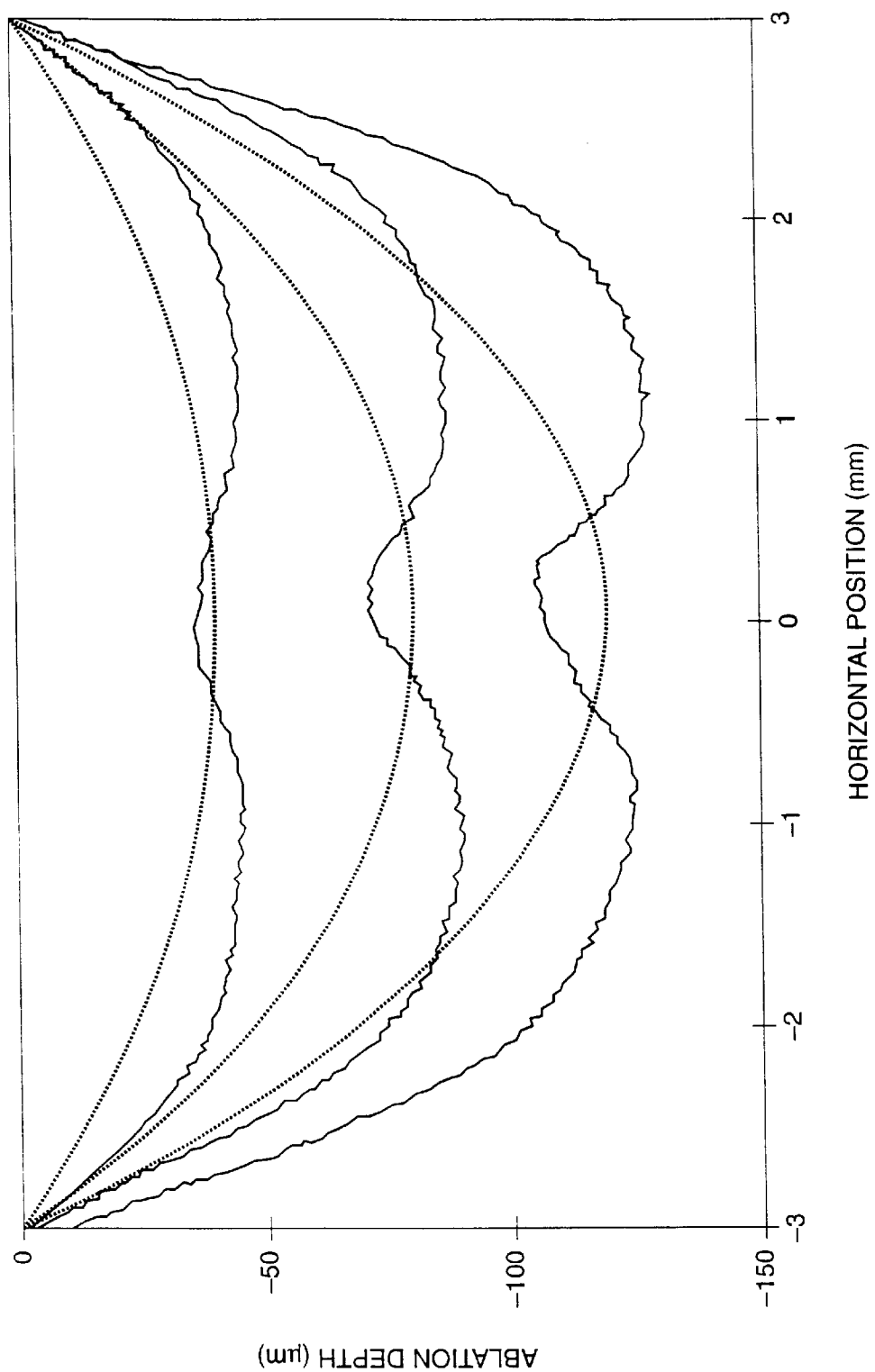
FIGS. 12A–16 illustrate alternative desired (dashed lines) and actual (solid lines) ablation profiles which may benefit from the present invention.
Figure 12B:
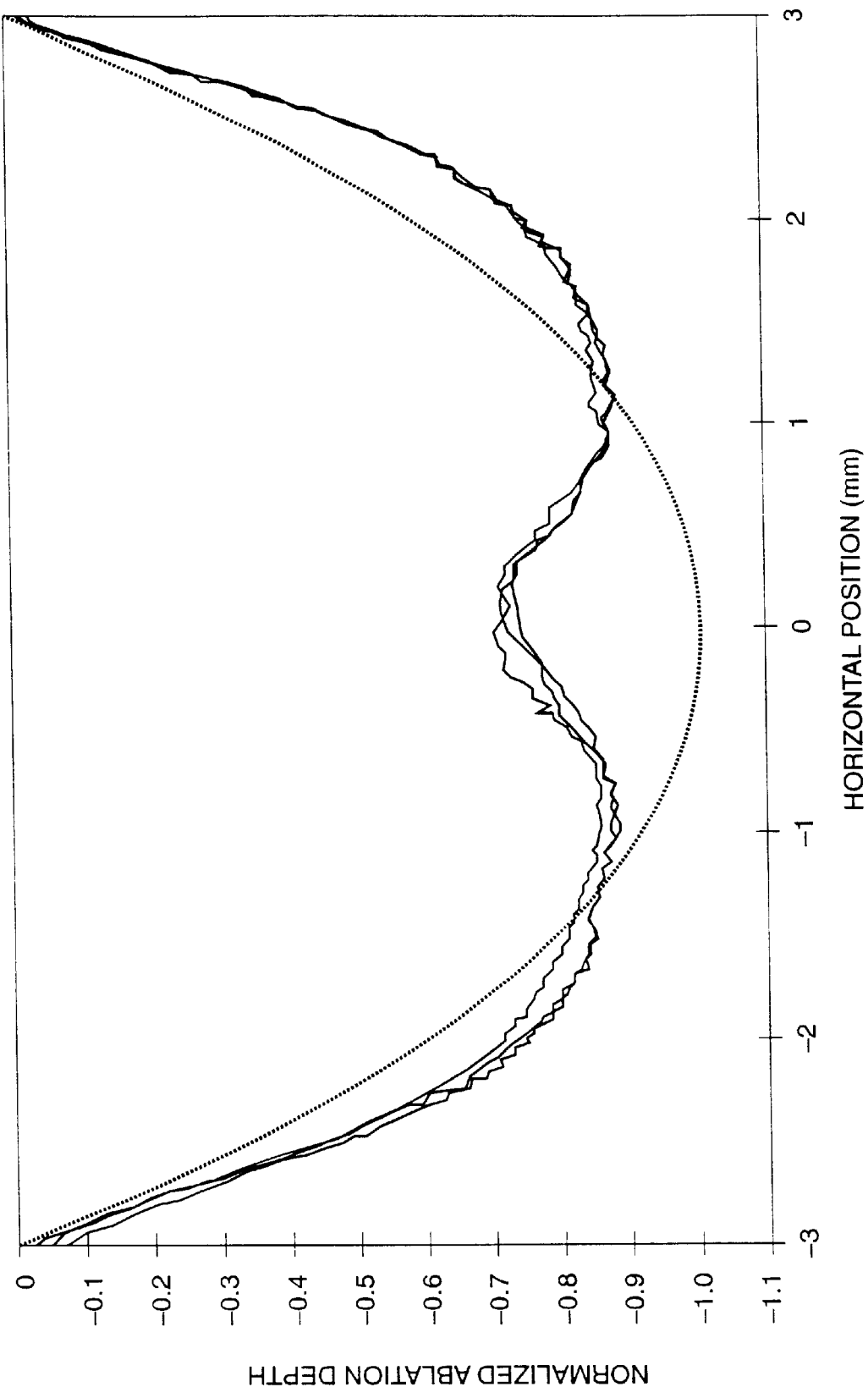
Figure 13A:
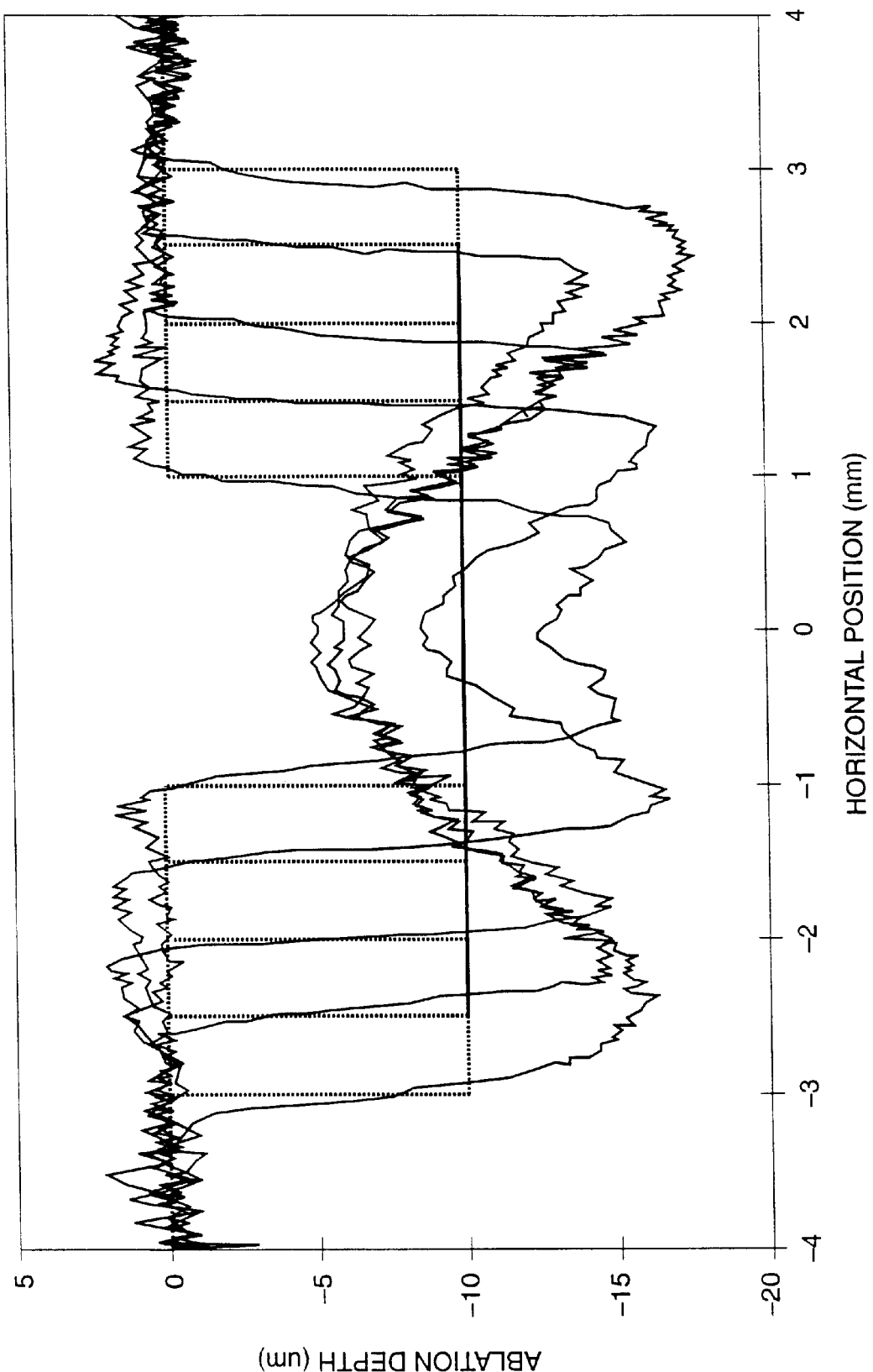
Figure 13B:
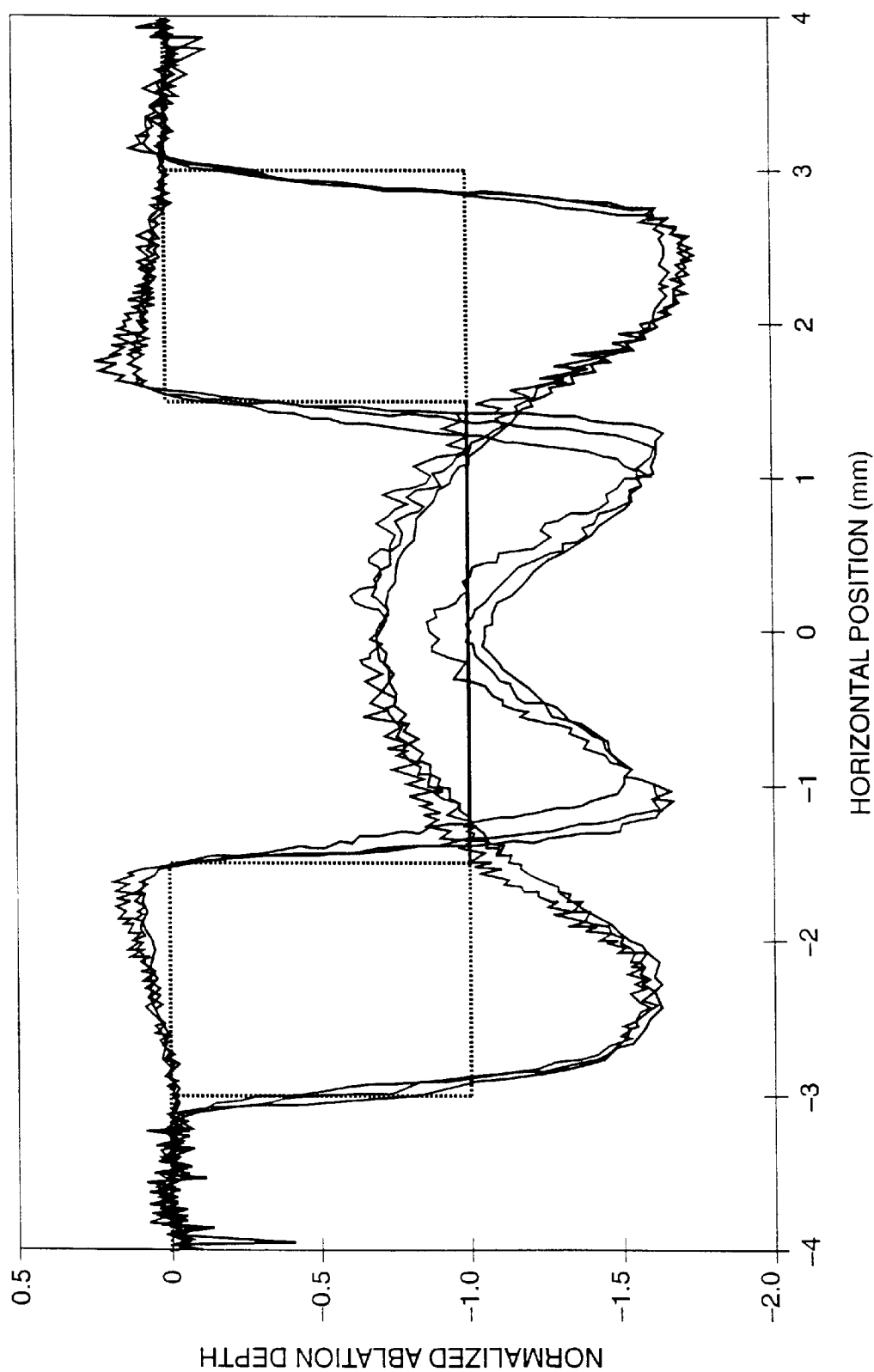
Figure 14:
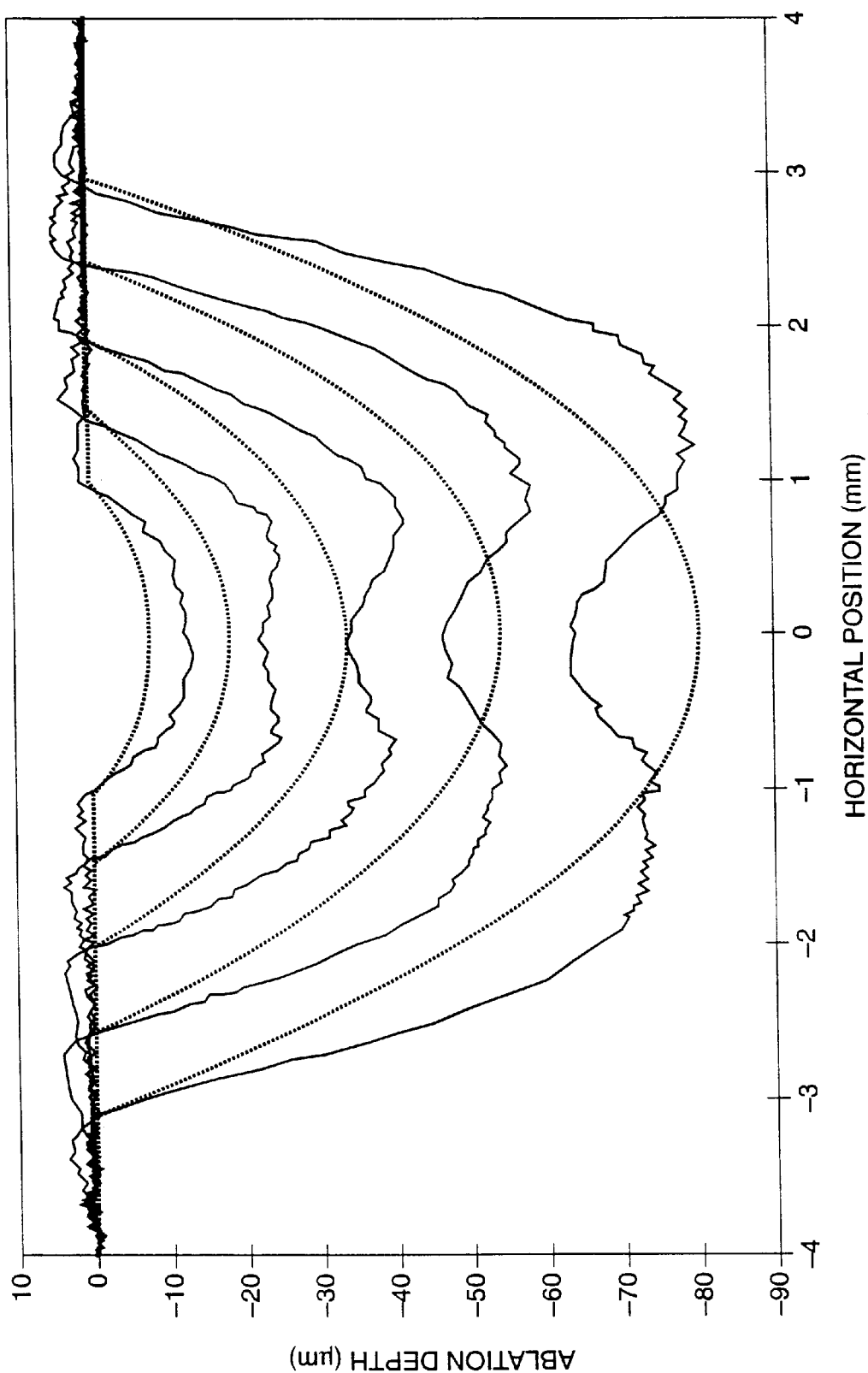
Figure 15:
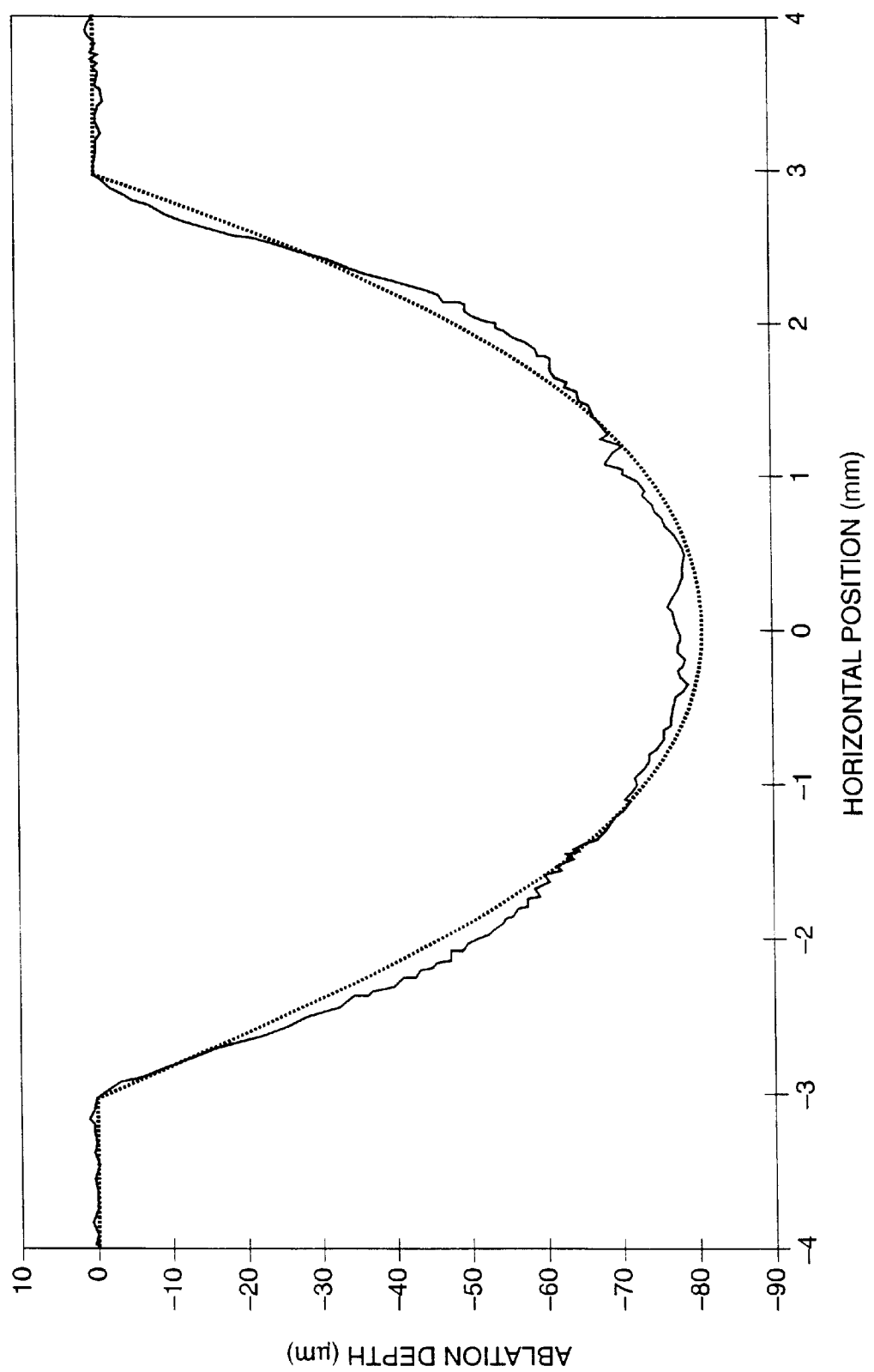
Figure 16:
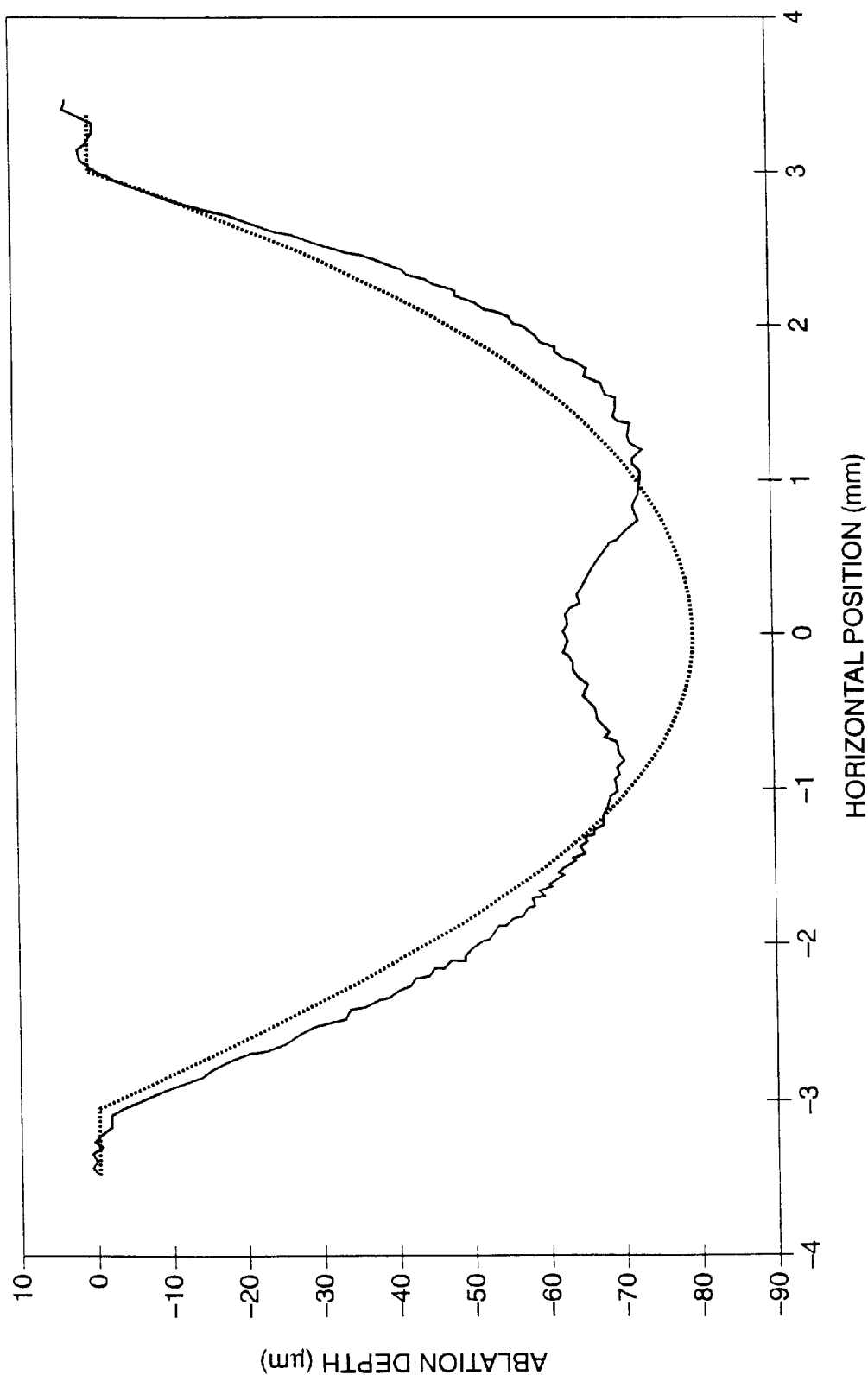

Referring to FIG. 9, a method for generating a direct, silhouette image of the anterior surface of the cornea during or immediately following a surgical procedure will now be described. The present invention may be used in conjunction with a wide variety of surgical procedures on the eye, and is particularly useful with laser ablation procedures, such as photorefractive keratectomy (PRK), phototherapeutic keratectomy (PTK), laser in-situ keratomileusis (LASIK) or the like. In such procedures, a laser is prepared to deliver the appropriate radiation in accordance with the calculated beam delivery parameters for the specific procedure, e.g., the power level and spatial location on the corneal surface. In PRK or PTK procedures, the epithelium is completely removed to expose the anterior region of the stroma. In LASIK procedures, the epithelium, Bowman's membrane and a portion of the anterior stroma are partially incised from the stroma and folded back to expose the stroma to the laser. The laser beam is typically controlled to impinge upon an area of the cornea of an eye to form therein a predetermined ablation shape. The laser selected for use preferably emits in the ultraviolet, namely at wavelengths of less than substantially 400.0 nm.

For convenience, the method will be described as applied to a laser photo ablation method (PRK) using an argon fluoride excimer laser which generates ultraviolet radiation at 193.0 nm at predetermined pulse energy densities and repetition rates. In an exemplary embodiment, a VISX STAR Excimer Laser System™ may be used for the ablation (commercially available from VISX, Inc. of Santa Clara, Calif.). This system produces an output of 193.0 nm, operates at a frequency of 6.0 Hz and is adjusted to deliver uniform fluency of 160.0 millijoules/cm$^2$ with a 6.0 mm diameter ablation zone. Other laser systems suitable for use with the present invention are the T-PRK® scanning and tracking laser from Autonomous Technologies Corporation, the SVS Apex laser from Summit Technology Inc., the Keracor™ 117 scanning laser system from Chiron Vision, or the like.

Figure 8:
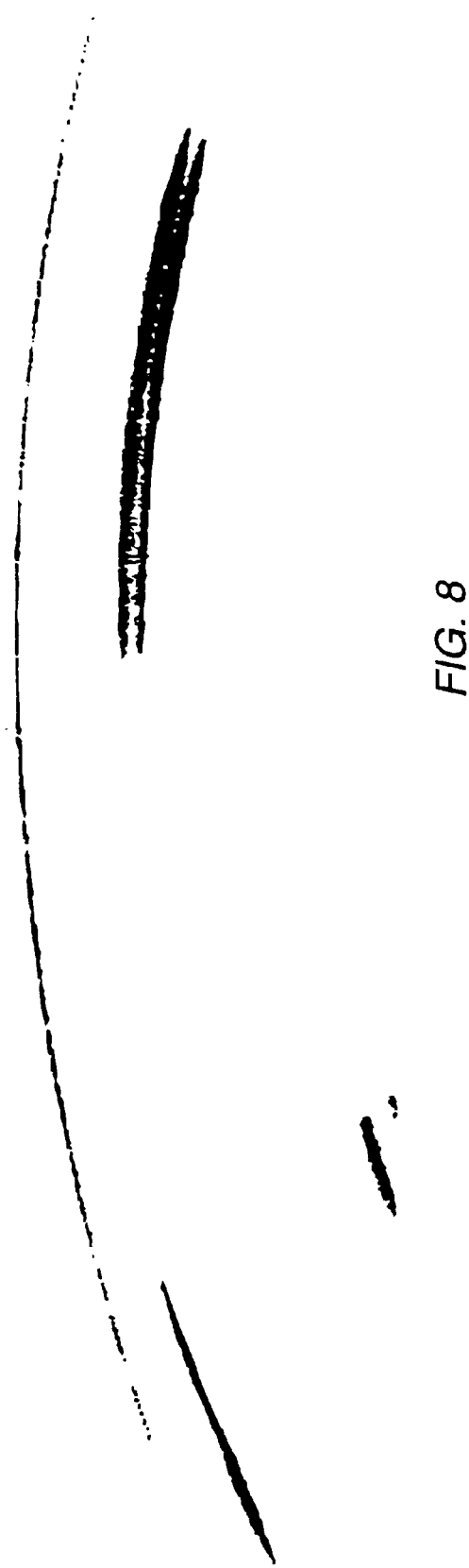
FIG. 8 schematically illustrates a method for generating images of the ablated corneal surface during a laser ablation procedure.

As shown in FIG. 8, a representative photoablation laser surgery apparatus and system 100 using the laser delivery system 102 and an associate power supply control system (not shown) pilots a laser beam 106 onto a cornea of an eye E. A microscope 116 with a viewing path coinciding with the laser beam may be used to align the laser beam with the optical axis of the eye, and for observing the laser ablation procedure. An aspirator (not shown) may be positioned above the ablation region to capture the plume as it lifts from the surface. PRK ablation algorithms are typically used to control the spatial and temporal distribution of the laser pulses. Suitable algorithms for use with the present invention are discussed in Munnerlyn, C. R., et al. *Photorefractive Keratectomy: A Technique For Laser Refractive Surgery. J. Cataract Refract. Surg.* (1988) 14:46–52. Other ancillary components of the laser surgery system 100 which are not necessary to an understanding of the invention have been omitted to avoid prolixity. Further details of suitable system and methods for performing a laser ablation procedure can be found in commonly assigned U.S. Pat. Nos. 4,665,913, 4,669,466, 4,732,148, 4,770,172, 4,773,414, 5,207,668, 5,108,388, 5,219,343 and 5,163,934, the complete disclosures of which are hereby incorporated herein by reference.

During or immediately following the laser ablation procedure, optical system 50 may be used to generate silhouette images of the ablated portions of the cornea. It will be appreciated that, for a number of reasons discussed above, the present invention allows these images to be generated without substantially interfering with the laser ablation process, or the surgeon's view of the site. To determine the ablation profile, a pre-ablation image is generated before radiation is delivered to the cornea to establish one or more reference images. These reference images are then registered with the postablation images to measure the shape of ablation across the cornea. Because slight amounts of eye motion can produce errors in the measured ablation, the corneal profiles are aligned using unablated portions of each profile prior to registration of the profiles.

As discussed above, each image will generally illustrate a single meridian of the cornea corresponding to the highest elevation of the cornea. However, in cases where the eye is irregular the highest elevation of the cornea measured may deviate from the intended meridian. Accordingly, a number of images may be taken of different meridians to generate a two or three dimensional image of the cornea. One method of accomplishing this is to provide an array of point light sources 150, such as LED's, in front of the eye. The point light sources 150 are illuminated sequentially. As the patient looks at each point light source 152 within the array 150, an image of the cornea will be generated. Alternatively, an eye tracking system may be used that automatically keeps track of the eye's position during the imaging processing. The eye tracking system will feed this information to the computer so that the position of the eye can be determined for each image. Suitable eye tracking systems are commercially available.

The images may be generated after the ablation procedure has been completed to determine the shape of tissue ablation rates and to evaluate the feasibility of changing the distribution of laser pulses during PRK. Alternatively, the images may be generated between laser pulses to determine the ablation geometry as the laser treatment proceeds. With this method, the information may be processed and fed into the ablation algorithm to provide feedback to modify the ablation algorithm. This information may be used immediately to improve the present procedure in situ, or it may be analyzed and used to modify the ablation algorithm for future treatments. For example, if the images indicate that a central island is being formed with the laser pulses, the computer may change the ablation algorithm to ablate more tissue in the central area of the cornea as can be understood with reference to FIGS. 10–16. This iterative process allows the surgeon to generate the appropriate depth of ablation of the specific procedure in situ or for later treatments.

Alternatively, if the amount of tissue removal is greater than anticipated, the programmed laser treatment may be decreased to avoid over correction. For example, if a –10D ablation is desired, the laser may be programmed to ablate a series of –1D ablations, with a measurement taken between each –1D ablation. After 9 –1D ablations, the profilometer may show –9.5D of ablation. Consequently, the laser is programmed to ablate –0.5D on the 10th ablation to achieve an improved result.

The present invention may be used to determine the ablation characteristics of the "average" human eye by compiling information from the images generated from a number of different eyes. Alternatively, the inventors have recognized that there are individual differences in the ablation characteristics of each person's eyes. Accordingly, the present invention may be used to determine the ablation characteristics of an individual eye so that the ablation algorithm may be customized for each individual eye. In yet another embodiment, a plurality of ablation profiles taken with the same laser may be compiled to calculate a laser treatment based on the ablation characteristics of that individual laser.

In addition, it should be noted that although the present invention has generally been described in use with a stationary laser system, it should be clearly understood that the invention is not limited to this type of system. For example, the systems and methods described herein may be employed in conjunction with a scanning laser system, such as the T-PRK® scanning and tracking laser from Autonomous Technologies Corporation or the Keracor™ 117 scanning laser system from Chiron Vision. With scanning laser systems, the images may be generated after the procedure is completed, or during the procedure. In the latter case, for example, images may be generated of the already scanned portions of the cornea, while the laser is completing ablation of the remaining portions of the cornea. The known laser characteristics of an individual laser may also be used to correct other laser of a similar configuration, particularly those of the same make and model.

What is claimed is:

1. An optical system comprising:
    a light source projecting light onto a reflective surface near a patient's eye to create reflected light such that at least a portion of the reflected light is passed across an anterior surface of the eye to illuminate a profile of the eye; and
    an image generating system including means for receiving the reflected light and generating a direct profile image of the anterior surface of the eye including a dark region representing the eye and a light region, the image generating system further comprising a processor for determining a line formed between the dark and light regions.

2. The optical system of claim 1 further comprising an aperture positioned along the optical path between the light source and the reflective surface, the aperture having a partially annular shaped opening for projecting a partially annular shaped light pattern onto the reflective surface.

3. The optical system of claim 1 wherein the light source emits light having a wavelength of between about 700 to 900 nanometers.

4. The optical system of claim 1 further comprising an aperture positioned between a lens and a photodetector, the lens focusing the projected light onto the aperture to increase a depth of field of the image.

5. The optical system of claim 1 wherein reflective surface uniformly scatters the reflected light.

6. The optical system of claim 1 wherein the reflective surface is positionable between the patient's eye and a lateral surface of the patient's nose.

7. The optical system of claim 1 wherein the image generating system comprises a photodetector and a lens positioned to receive the reflected light from the reflective surface and to image the reflected light onto the photodetector.

8. The optical system of claim 7 wherein the image generating system further comprises means for processing signals from the photodetector and for generating the direct profile image of the anterior surface of the eye corresponding to said signals.

9. The optical system of claim 1 further comprising an eye positioning assembly for determining a position and orientation of a selected region of the eye.

10. The optical system of claim 9 wherein the eye positioning assembly comprises an array of point light sources located at predetermined positions with respect to the eye.

11. The optical system of claim 1 wherein the processor has edge detection software for determining the line between the dark and light regions.

12. The optical system of claim 11 further comprising a memory for storing a pre-ablation profile image of the anterior surface of the eye, and means for registering the direct profile image with the pre-ablation profile image to determine an actual depth of tissue ablation.

13. The optical system of claim 12 wherein the means for generating the direct profile image includes means for providing the direct profile image with sufficient data points to determine the actual depth of tissue ablation when the actual depth of tissue ablation is less than 20.0 $\mu$m.

14. The optical system of claim 1 further comprising a reflector having the reflective surface and configured for positioning adjacent to the patient's eye.

15. An optical system comprising:
    a laser assembly for projecting radiation onto a selected region of an anterior surface of a cornea to effect ablation of said selected region to a certain depth;
    a light projecting assembly for projecting light onto a reflective surface near a patient's eye to create reflected light such that at least a portion of the reflected light is passed across the anterior surface of the selected region to illuminate a profile of the cornea; and
    an image generating assembly including means for generating a direct profile image of the selected region of the cornea during or immediately following ablation of said selected region.

16. The optical system of claim 15 wherein the direct profile image is generated with the selected region directly exposed to the ambient environment and without applying a substance to the selected region of the anterior surface.

17. The optical system of claim 15 further comprising a processing assembly, a memory for storing a pre-ablation profile image of the selected region, and means for registering the direct profile image with the preablation profile image to determine an actual depth of tissue ablation within the selected region.

18. The optical system of claim 17 wherein the processing assembly includes means for comparing the direct profile image with a reference ablation profile image and means for calculating a laser ablation algorithm based on differences between the direct profile image and the reference ablation profile image.

* * * * *